United States Patent
Amoabediny et al.

(10) Patent No.: US 11,419,957 B2
(45) Date of Patent: Aug. 23, 2022

(54) AUTOMATED DEVICE FOR PRODUCTION OF BIOENGINEERED TISSUES AND ORGANS BASED ON DECELLULARIZATION AND RECELLULARIZATION

(71) Applicants: Ghassem Amoabediny, Tehran (IR); Seyed Hossein Mahfouzi Mousavi, Tehran (IR); Seyed Hamid Safiabadi Tali, Tehran (IR); Mostafa Ghanei, Tehran (IR)

(72) Inventors: Ghassem Amoabediny, Tehran (IR); Seyed Hossein Mahfouzi Mousavi, Tehran (IR); Seyed Hamid Safiabadi Tali, Tehran (IR); Mostafa Ghanei, Tehran (IR)

( * ) Notice: Subject to any disclaimer, the term of this patent is extended or adjusted under 35 U.S.C. 154(b) by 282 days.

(21) Appl. No.: 16/820,554

(22) Filed: Mar. 16, 2020

(65) Prior Publication Data
US 2021/0283292 A1    Sep. 16, 2021

(51) Int. Cl.
*A61L 2/24* (2006.01)
*A61L 27/36* (2006.01)
(Continued)

(52) U.S. Cl.
CPC ............. *A61L 2/24* (2013.01); *A61L 2/202* (2013.01); *A61L 2/206* (2013.01); *A61L 2/26* (2013.01); *A61L 27/3683* (2013.01); *A61L 2202/121* (2013.01); *A61L 2202/122* (2013.01); *A61L 2202/14* (2013.01); *A61L 2202/15* (2013.01);
(Continued)

(58) Field of Classification Search
CPC ... A61L 2/18; A61L 2/20; A61L 2/202; A61L 2/206; A61L 2/24; A61L 2/26; A61L 27/3683; A61L 2202/121; A61L 2202/122; A61L 2202/123; A61L 2202/14; A61L 2202/15; A61L 2430/20; A61L 2430/26; A61L 2430/28; A61L 2430/40; C12M 21/08; C12M 29/10; C12M 37/00
See application file for complete search history.

(56) References Cited

U.S. PATENT DOCUMENTS

| | | | | |
|---|---|---|---|---|
| 5,989,913 A | * | 11/1999 | Anderson | C12M 27/10 435/293.1 |
| 7,439,057 B2 | * | 10/2008 | Frangos | C12M 25/02 435/395 |

* cited by examiner

*Primary Examiner* — Timothy C Cleveland (57) ABSTRACT

The present invention discloses an automated device for tissue and organ engineering. The device comprises a main chamber for performing decellularization, tissue sterilization, and recellularization and a set of solution and medium chambers, which provide solutions and medium for the decellularization and recellularization processes, respectively, in a continuous closed circuit. The device further comprises a sterilizing system for self-sterilization of the automated device. The device further comprises a user interface to input steps of protocols for tissue or organ engineering. The device further comprises a controller configured to control valves and pumps, which control and direct the flow of solutions and medium based on the steps of protocols, thereby automating the processes of decellularization, tissue sterilization, recellularization and self-sterilization. All parts of the device are installed in one single body in a fully integrated manner, in one example, which makes the device ready to use. The device minimizes the user intervention and enhances sterility, reproducibility, and efficiency.

20 Claims, 3 Drawing Sheets

(51) Int. Cl.
*A61L 2/26* (2006.01)
*A61L 2/20* (2006.01)
(52) U.S. Cl.
CPC ....... *A61L 2430/20* (2013.01); *A61L 2430/26* (2013.01); *A61L 2430/28* (2013.01); *A61L 2430/40* (2013.01)

AUTOMATED DEVICE FOR PRODUCTION OF BIOENGINEERED TISSUES AND ORGANS BASED ON DECELLULARIZATION AND RECELLULARIZATION

BACKGROUND OF THE INVENTION

Tissue engineering involves the use of a tissue scaffold for the formation of new viable tissues for transplantation or in vitro monitoring of drug toxicity in model disease tissues. Tissue engineering, which uses elements including cells, scaffolds, and growth factors to fabricate functional organs in vitro, is a promising strategy to mitigate the scarcity of transplantable organs. In recent years, different construction strategies that guide the combination of tissue engineering elements have been applied in solid organ tissue engineering and have achieved much progress. Recently, a construction strategy based on whole-organ decellularization has become a popular and promising approach.

However, despite the preservation of the whole structure, the current constructs derived from decellularization-based strategies still perform partial functions of organs, due to several challenges, including preservation of functional extracellular matrix structure, implementation of functional recellularization, the formation of functional vascular network, organ sterilization, and realization of long-term functional integration.

One of the key factors that prevents advancement of the field is the lack of an ideal transplantable scaffold that has all the necessary microstructure and extracellular cues for cell attachment, differentiation, functioning, as well as vascularization, which has so far proven to be difficult to manufacture in vitro. Further, failure of organs such as heart, liver, kidney, cartilages and etc., is a major cause of the world's mortality due to a critical shortage of donor organs.

Henceforth, there is a need for an automated device for producing tissues/organs industrially and automatically based on decellularization and recellularization technologies. Further, there is also a need for an integrated and automated device for efficiently performing different functions include decellularization, recellularization, tissue sterilization, and self-sterilization processes.

SUMMARY OF THE INVENTION

The present invention discloses an automated device for producing bioengineered tissues/organs in a facilitated and integrated manner. The device integrates a plurality of equipment within a single unit to perform the processes of decellularization, tissue sterilization, recellularization, and self-sterilization automatically based on user-defined protocols.

The device comprises a main chamber to contain various sizes of tissues and perfuse the tissues for decellularization, tissue sterilization, or recellularization processes. The main chamber includes at least one solution inlet, at least one solution outlet, at least one medium inlet, at least one medium outlet, at least one gas inlet, and at least one gas outlet. The device further comprises at least one solution chamber to contain a solution liquid for the decellularization and tissue sterilization processes. The device further comprises at least one medium chamber containing the medium or medium solution for the recellularization process. The device also includes a waste chamber designed to receive the waste liquid. In one embodiment, the solution inlet and the solution outlets form a closed loop for continuously circulating the liquid solution within the main chamber for effectively perfusing the tissue, for example, the lung.

The device further comprises at least one solution conduit to deliver the solution liquid from at least one solution chamber to the main chamber through the at least one solution inlet. The device further comprises at least one medium conduit to deliver medium from at least one medium chamber to the main chamber through the at least one medium inlet. The device further comprises at least one waste conduit to deliver the waste liquid from the main chamber to the waste chamber through the at least one solution outlet.

Also, the device comprises a sterilizing system having at least one sterilizing source. The at least one sterilizing source is applied to sterilize at least one solution conduit, at least one medium conduit, and at least one waste conduit. Also, the device comprises at least one inlet gas conduit designed to deliver gas flow from a gas source into the main chamber and at least one outlet gas conduit to discharge gas from the main chamber.

The device further comprises at least one solution valve for controlling solution flow into the tissue and at least one solution pump for directing the solution liquid into the tissue. Furthermore, the device comprises at least one medium valve configured to control medium flow into the tissue and at least one medium pump configured to direct the medium into the tissue. Also, the device comprises at least one inlet gas valve configured to control gas flow into the main chamber and at least one outlet gas valve configured to control gas flow out of the main chamber. Also, the device comprises at least one waste valve configured to control waste flow into the waste chamber and at least one waste pump configured to direct the waste flow into the waste chamber. The device also includes at least one sterilizing valve to control the sterilizing fluid flow.

The device further comprises a control system having a controller for automatically implementing user-defined protocols for performing the processes of decellularization, tissue sterilization, recellularization, and self-sterilization. The controller is configured to receive the steps of a protocol for perfusing the tissue and control at least one solution valve, at least one medium valve, at least one waste valve, at least one sterilizing valve, at least one solution pump, at least one medium pump, or at least one waste pump for performing all steps of the tissue decellularization, sterilization, recellularization, or self-sterilization protocols.

One aspect of the present disclosure is directed to an automated device for tissue and organ engineering, comprising: a) a main chamber having at least one solution inlet, at least one solution outlet, at least one medium inlet, at least one medium outlet, at least one gas inlet, and at least one gas outlet, wherein the main chamber is configured to receive and culture tissue in a sterile and sealed environment; b) at least one solution chamber fluidly connected to the main chamber through at least one solution conduit, at least one solution valve, and at least one solution pump, wherein the at least one solution chamber is configured to contain liquid solution for decellularization and tissue sterilization process; c) at least one medium chamber fluidly connected to the main chamber through at least one medium conduit, at least one medium valve, and at least one medium pump, wherein the at least one medium chamber is configured to contain a medium solution for recellularization processes; d) at least one waste chamber fluidly connected to the main chamber through at least one waste conduit, at least one waste pump and at least one waste valve, wherein the waste chamber is configured to receive waste liquid from the main chamber, the at least one solution chamber, and the at least one medium chamber; e) a sterilizing system includes at least one sterilization source containing at least one of sterilizing gas and sterilizing liquid, wherein the at least one sterilization source is fluidly connected to the at least one solution conduit, at least one medium conduit, and at least one waste conduit through at least one sterilization valve, wherein the sterilizing gas is at least any one of ozone and ethylene oxide; f) a controller configured to control at least one solution valve, at least one medium valve, at least one waste valve, at least one sterilizing valve, at least one solution pump, at least one medium pump, and at least one waste pump; and g) a user interface in communication with the controller configured to allow a user to input protocol to perform decellularization, tissue sterilization, recellularization, and self-sterilization process, wherein the controller is configured to automatically implement the protocol for performing the decellularization, tissue sterilization, recellularization, and self-sterilization process. In one embodiment, the device comprises a single body wherein all parts are installed in a fully integrated manner.

In one embodiment, the tissue is perfused through one or more embedded ports based on the input protocol. In another embodiment, the device further comprises at least one gas source fluidly connected to the main chamber through at least one gas conduit, wherein the inlet gas valve controls the flow of gas into the main chamber. In one embodiment, the gas is at least any one of oxygen, carbon dioxide, and nitrogen. In another embodiment, the gas source is at least any one of a gas generator, a capsule, and a gas compressor. In one embodiment, the at least one solution chamber is at least one of a carboy and a syringe. In another embodiment, the liquid solution includes at least any one of phosphate-buffered saline (PBS), sodium dodecyl sulfate (SDS), and TRITON X-100™ for decellularization process.

In one embodiment, the liquid solution includes at least one of penicillin and streptomycin for the tissue sterilization process. In another embodiment, the at least one solution valve is a solenoid pinch-type valve. In one embodiment, the at least one solution pump is a peristaltic pump. In another embodiment, the solution inlet and the solution outlet of the main chamber form a closed loop for continuously circulating the liquid solution within the main chamber for effectively perfusing the tissue. In another embodiment, the medium inlet and the medium outlet of the main chamber form a closed loop for continuously circulating the medium solution within the main chamber for effectively perfusing the tissue.

Another aspect of the present disclosure is directed to an automated device for tissue and organ engineering, comprising: a main chamber having at least one solution inlet, at least one solution outlet, at least one medium inlet, at least one medium outlet, at least one gas inlet, and at least one gas outlet, wherein the main chamber is configured to receive and culture tissue in a sterile and sealed environment; at least one solution chamber fluidly connected to the main chamber through at least one solution conduit, at least one solution valve, and at least one solution pump, wherein the at least one solution chamber is configured to contain liquid solution for decellularization and tissue sterilization process, wherein the solution inlet and the solution outlet form a closed loop for continuously circulating the liquid solution within the main chamber for effectively perfusing the tissue; at least one medium chamber fluidly connected to the main chamber through at least one medium conduit, at least one medium valve, and at least one medium pump, wherein the at least one medium chamber is configured to contain medium solution for recellularization processes, wherein the medium inlet and medium outlet form a closed loop for continuously circulating the medium solution within the main chamber for effectively perfusing the tissue; at least one waste chamber fluidly connected to the main chamber through at least one waste conduit, at least one waste pump and at least one waste valve, wherein the waste chamber is configured to receive a waste liquid from the main chamber, the at least one solution chamber, and the at least one medium chamber; a sterilizing system includes at least one sterilization source containing at least one of sterilizing gas or sterilizing liquid, wherein the at least one sterilization source is fluidly connected to the at least one solution conduit, at least one medium conduit, and at least one waste conduit through at least one sterilization valve; a controller configured to control at least one solution valve, at least one medium valve, at least one waste valve, at least one sterilizing valve, at least one solution pump, at least one medium pump, and at least one waste pump; and a user interface in communication with the controller configured to allow a user to input protocol to perform decellularization, tissue sterilization, recellularization, and self-sterilization process, wherein the controller is configured to automatically implement the protocol for performing the decellularization, tissue sterilization, recellularization, and self-sterilization process.

In one embodiment, the device further comprises at least one gas source fluidly connected to the main chamber through at least one gas conduit, wherein the inlet gas valve controls flow of gas into the main chamber, wherein the gas is at least any one of oxygen, carbon dioxide, and nitrogen, and wherein the gas source is at least any one of a gas generator, a capsule, and a gas compressor. In another embodiment, the sterilizing gas is at least any one of ozone and ethylene oxide.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

The present invention generally relates to a tissue and organ engineering device, and more particularly relates to a device for production of bioengineered tissues and organs based on decellularization and recellularization technologies.

A description of embodiments of the present invention will now be given with reference to the figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Figure 1:
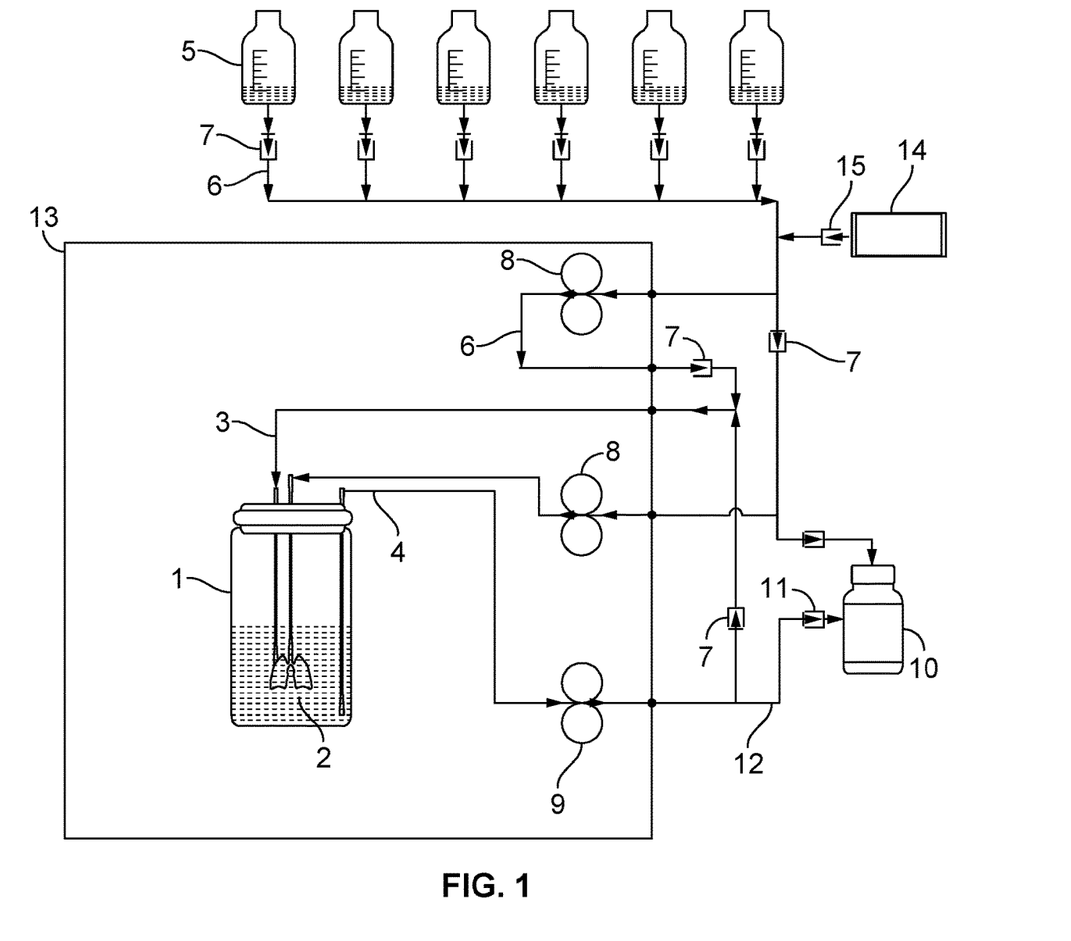
FIG. 1 illustrates a block diagram of an automated device for producing of bioengineered tissues and/or organs, according to one embodiment.

Referring to FIG. 1, a block diagram of an automated device configured to perform a decellularization process according to one embodiment of the present invention. In one embodiment, the device is configured to develop tissues and/or organs by efficiently performing different functions include decellularization, recellularization, tissue sterilization, self-sterilization processes. In one embodiment, the device comprises at least one main chamber 1, at least one or more solution chambers 5, at least one waste chamber 10, and a sterilizing system.

In one embodiment, the main chamber 1 is configured to receive and culture a tissue 2 in a sterile and sealed environment. The main chamber 1 provides and maintains a sterile and seal environment to perfuse the tissue 2. In an exemplary embodiment, the tissue 2 could be, but not limited to, lung tissues. In one embodiment, the device could be used for any tissue which could be perfused, such as the heart, kidney, and liver. In addition, the device may be used to perfuse a whole organ or a part of an organ. Thus, the term "tissue" is applicable to whole organs and any functional parts of the organ, such as a lobe of a lung.

In one embodiment, the main chamber 1 is made of, but not limited to, a transparent material. In one embodiment, the main chamber 1 is further comprises at least one solution inlet 3 and a solution outlet 4. In one embodiment, the solution inlet 3 and the solution outlets 4 form a closed loop for continuously circulating the liquid solution within the main chamber for effectively perfusing the tissue 2, for example, the lung. To do so, the waste pump 9 directs the liquid solution in the main chamber 1 to the solution inlet 3 through solution conduits 6.

In one embodiment, the solution chambers 5 are fluidly connected to the main chamber 1 through at least one solution conduit 6, one or more solution valves 7, and one or more solution pumps 8. The solution valves 7 and solution pumps 8 are placed between the solution chambers 5 and the main chamber 1. The solution chambers 5 are configured to contain a liquid solution for the decellularization process. The liquid solution could be in the form of emulsion or suspension. In one embodiment, the liquid solution is at least any one of, but not limited to, phosphate-buffered saline (PBS), sodium dodecyl sulfate (SD S), and TRITON X-100'. In one embodiment, the solution chambers 5 is at least any one of a suitable container, but not limited to, a carboy and a syringe, and the like.

In one embodiment, the solution valves 7 could control the flow of the liquid solution from a specified solution chamber 5 to the main chamber 1. The solution valves 7 may be of any valves with any appropriate mechanism which can control the flow of the liquid solution from a solution chamber 5 to a solution inlet 3, thereby enhancing sterility. In one embodiment, the solution valves 7 could be, but not limited to, solenoid pinch-type valves.

The solution pumps 8 direct the flow of the liquid solution from a certain solution chamber 5 to the main chamber 1 via the solution inlet 3. In one embodiment, the solution pumps 8 could be, but not limited to, a peristaltic pump, which is able to provide the flow in a sterile condition through the solution conduits 6. The solution conduits 6 are made of any suitable material that capable to transfer the liquid solutions and biomaterials while maintaining a sterile connection between the solution chambers 5 and the main chamber 1, such as, but not limited to, silicon or the like.

In one embodiment, the waste chamber 10 is fluidly connected to the main chamber 1 through at least one waste conduit 12. The waste chamber 10 is configured to receive a waste liquid from the main chamber 1, the solution chambers 5, via the waste conduit 12 and the solution conduit 6, respectively, using at least one waste pump 9 via at least one waste valve 11. The solution outlet 4 could be used as a waste outlet. In one embodiment, the sterilizing system includes at least one sterilization source 14. The sterilization source 14 contains at least one of sterilizing gas or sterilizing liquid. The sterilization source 14 is fluidly connected to the at least one solution conduit 6 and at least one waste conduit 12 through at least one sterilization valve 15.

In one embodiment, the device is further configured to perform a tissue sterilization process. In one embodiment, a method for sterilizing the tissue or organ 2, for example, lung using the device includes the following steps. At one step, the main chamber 1 is filled with the liquid solution such as sterilizing liquid includes, but not limited to, penicillin or streptomycin using the solution pump 8 via the solution conduit 6. In another embodiment, the liquid solution is used for the tissue sterilization process. In another embodiment, the liquid solution is at least any one of, but not limited to, penicillin and streptomycin. At another step, the tissue 2, for example, the lung is perfusing within the main chamber 1 by circulating the liquid solution via the closed-loop. The tissue 2, for example, the lung is perfused through one or more embedded ports based on the input protocol. Further, at another step, the liquid solution could be drained to the waste chamber 10 via the waste conduit 12 using the waste pump 9.

Figure 2:
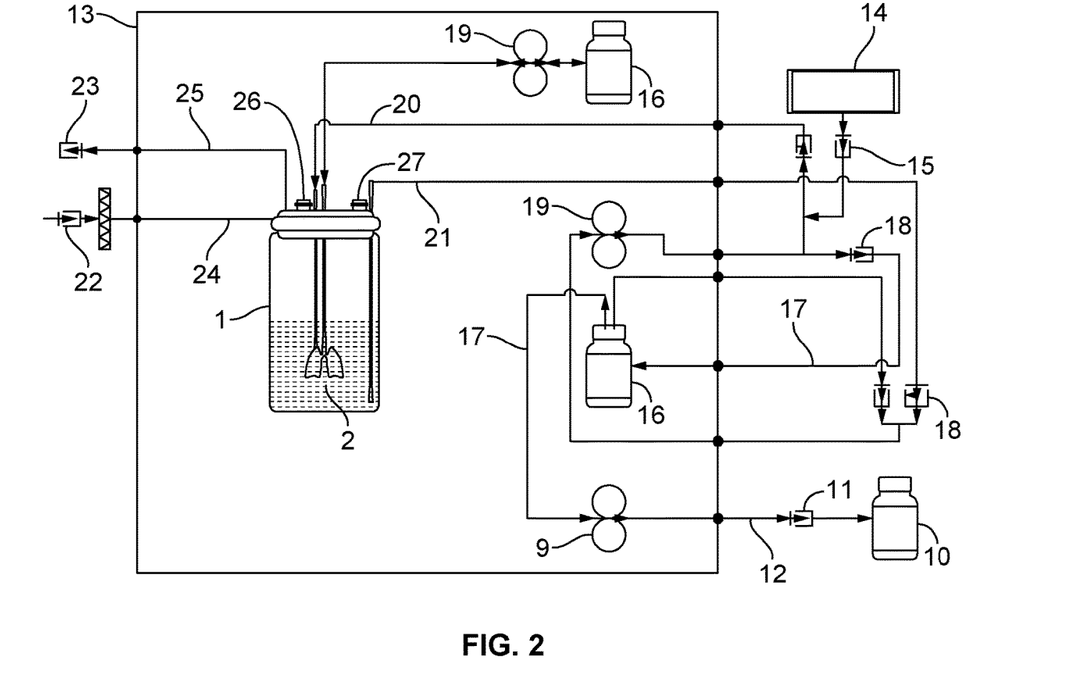
FIG. 2 illustrates a block diagram of an automated device for producing of bioengineered tissues and/or organs, according to one embodiment.

In one embodiment, a controller or a control system 40 (shown in FIG. 3) is configured to control, but not limited to, the solution valves 7, solution pumps 8, waste pumps 9, waste valves 11, the sterilizing valve 15, gas valves (22 and 23) (shown in FIG. 2). In one embodiment, the controller 40 is configured to automatically implement the protocol for performing the decellularization, tissue sterilization, recellularization, and self-sterilization processes. This automation is done through controlling valves and pumps which control and direct the flows of the liquid solution and medium solutions based on the steps of protocols. With fully automating the processes of decellularization, tissue sterilization, and recellularization, the direct intervention of the user is minimized resulting in enhanced sterility, reproducibility, and efficiency, which finally increases the possibility of producing a reliable, functional organ which could be used for implantation. In one embodiment, a user interface 41 (shown in FIG. 3) is provided for a user for operating the device, and may be coupled to the controller 40. The user interface 41 in communication with the controller configured to allow a user to input protocols to perform decellularization, tissue sterilization, recellularization, and self-sterilization processes.

In one embodiment, the device is further configured to perform self-sterilization. It can direct the materials and liquids in the different conduits to the waste chamber 10 based on the user will, for example, after finishing each of the decellularization or recellularization processes. The materials and liquids could be drained to the waste chamber 10 via the waste conduit 12 using the waste pump 9. The sterilizing system includes a sterilizing gas or liquid source 14 and a sterilization valve 15 which controls the connection of the sterilizing source to the conduits.

The sterilizing gas or liquid may be of any appropriate type of material used for sterilization such as, but not limited to, ozone and ethylene oxide. The sterilizing source 14 is used for the sterilization of at least one solution conduit 6, at least one medium conduit 17, and at least one waste conduit 12. Also, the conduits are designed such that the sterilizing gas or liquid be able to penetrate all conduits. Moreover, all the parts of the device including the main chamber, solution chambers, medium chambers, and conduits are autoclavable. In one embodiment, all the parts of the device including the main chamber, solution chambers, medium chambers, and conduits are autoclavable, and wherein different tissues or organs such as lung, heart, liver, and kidney of various sizes are processed using the device.

In one embodiment, the device components such as, but not limited to, the main chamber 1, the solution inlet 3, solution outlet 4, the solution conduit 6, the solution pump 8, the waste pump 9 are securely integrated and positioned in a box-like structure 13. In one embodiment, a temperature sensor 30 (shown in FIG. 3) is disposed within the box-like structure 13 to measure the temperature.

Referring to FIG. 2, the device configured to perform the recellularization process in one embodiment of the present invention. In one embodiment, the device is further configured to perform the recellularization process for regenerating the tissue 2, for example, lung. In one embodiment, the main chamber 1 further comprises at least one medium inlet 20 and at least one medium outlet 21. In one embodiment, the device further comprises, at least one or more medium chambers 16.

The medium chambers 16 are fluidly connected to the main chamber 1 through the medium inlet 20 and medium outlet 21 via at least one or more medium conduits 17, one or more medium valves 18, and at least one or more medium pumps 19. In one embodiment, the medium chambers 16 are configured to contain a medium solution for recellularization processes. In one embodiment, the medium inlet 20 and medium outlet 21 form a closed loop for continuously circulating the medium solution within the main chamber 1 for effectively perfusing the tissue.

In one embodiment, the medium chambers 16 may be of any appropriate type of reservoirs such as, but not limited to, carboys, syringes and similar reservoirs for containing the medium solution. The medium conduits 17 may be of any common and appropriate material for transferring the medium solution and biomaterials, which is able to preserve the sterility of the connections between the main chamber 1 and the medium chambers 16 such as, but not limited to, silicon and similar materials. The medium valves 18 and medium pumps 19 are placed between the medium chambers 16 and the main chamber 1. The medium valves 18 control the flow of the medium solution from the medium chambers 16 to the main chamber 1 containing the tissue 2. The medium valves 18 could be any valves with a suitable mechanism to control the flow of the medium solution from a medium chamber 16 to a medium inlet 20. In one embodiment, the medium valves 18 could be, but not limited to, solenoid pinch-type valves, which control the flow of the medium solution without any direct contact with the fluid in the conduits resulting in enhanced sterility.

The medium pumps 19 are connected to the medium valves 18 through the medium conduits 17. The medium pumps 19 direct the flow of the medium solution from a specified medium chamber 16 to the main chamber 1 via the medium inlet 20. The medium pumps 19 may be of any type with an appropriate mechanism for pumping the liquid into the main chamber 1. In one embodiment, the medium pumps 19 could be, but not limited to, a peristaltic pump allowing for providing fluid flow through the medium conduits 17 while preserving the liquid sterility.

In one embodiment, the main chamber 1 further connected to at least one gas source through an inlet gas conduit 24 and an outlet gas conduit 25 using an inlet gas valve 22 and an outlet gas valve 23. The inlet gas valve 22 is placed between the main chamber 1 and the gas source, which controls the inlet gas flow into the main chamber 1 through the inlet gas conduit 24. The outlet gas valve 23 is placed between the main chamber 1 and the surrounding environment which controls the outlet gas flow from the main chamber 1 through the outlet gas conduit 25. In one embodiment, the gas source may contain any gas phase components such as, but not limited to, oxygen, carbon dioxide, nitrogen, or the like. In one embodiment, the gas source could be any gas containers or gas generators such as, but not limited to, capsules, gas compressors, or the like.

In one embodiment, the medium inlet 20 and medium outlet 21 form a closed loop for continuously circulating the medium solution within the main chamber 1 for effectively perfusing the tissue. The closed loop is designed such that the liquid in the main chamber 1 is taken out from a medium outlet 21 and enters into a medium inlet 20 allowing recirculation of the medium through the tissue 2. The medium pump 19 directs the liquid in the main chamber 1 into a medium inlet 20 through the medium conduits 17. In one embodiment, the device further comprises a plurality of sensors include, but not limited to, an oxygen sensor 26 and a pH sensor 27, and a temperature sensor 30. In some embodiments, the device further comprises, but not limited to, a heater 31, carbon dioxide sensors, weight sensors, pressure sensors, glucose measurement devices, and optical sensors.

Figure 3:
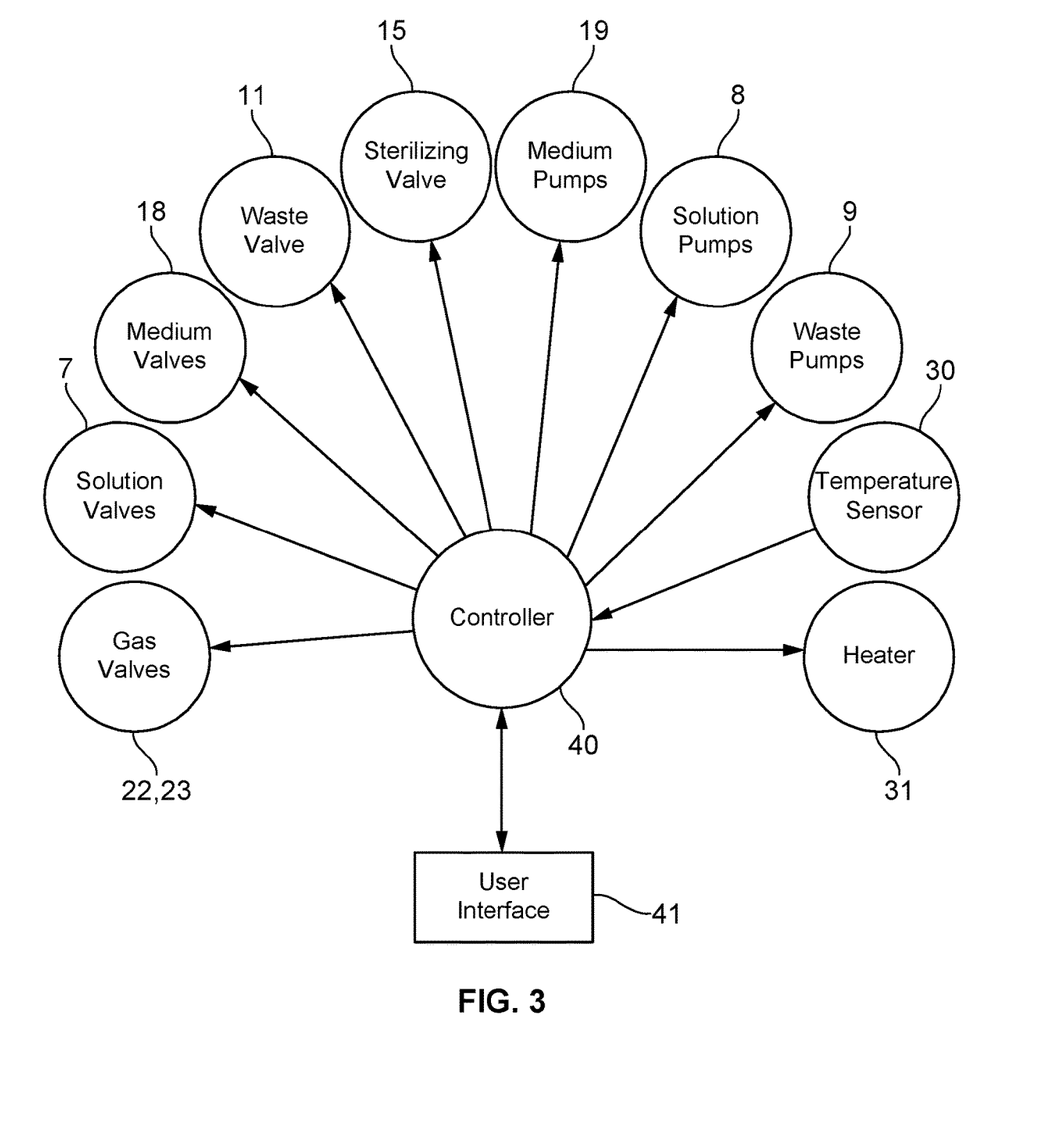
FIG. 3 illustrates a perspective view of a controller for controlling components, valves, and a user interface of the automated device according to one embodiment.

Referring to FIG. 3, the controller 40 coupled electronically and configured to control multiple components of the device is disclosed. In one embodiment, the controller 40 is configured to control at least one solution valve 7, at least one medium valve 18, at least one waste valve 11, at least one sterilizing valve 15, at least one solution pump 8, at least one medium pump 19, at least one waste pump 9, and the inlet gas valve 22 and the outlet gas valve 23. In one embodiment, the controller 40 in communication with the plurality of sensors, but not limited to, oxygen sensor 26, the pH sensor 27, the temperature sensor 30, and the heater 31. In one embodiment, the device is further configured to control the temperature based on a user-defined value and the data obtained by the temperature sensor 30.

In one embodiment, the user interface 41 could be securely integrated to the device. In one embodiment, the user interface 41 in communication with the controller 40 is configured to enable the user to input protocols to perform decellularization, tissue sterilization, recellularization, and self-sterilization process. The protocols may be of any known protocol used for tissue decellularization and recellularization or be any new protocol. The protocols may be saved on the controller 40 and be selected and used by the user later. Also, the saved protocols may be modified by the user. The user interface 41 allows the user to define steps of a protocol which includes operational information for valves and pumps. The protocol defined by the user is connected to the different parts of the device by the controller 41 allowing to run the protocols in the user-defined period. In one embodiment, the user interface 41 could be, but not limited to, a touch screen or a panel board.

The advantages of the present invention are disclosed as follows. The present device is fully integrated; that is, all the equipment such as main chamber 1, chambers, pumps, valves, and conduits are installed in a single body, which is delivered to customers in a ready-to-use form. This unique feature minimizes the need for assembling the device before each run, which facilitates its use. Furthermore, the integrity of the device results in reduced time for running the various processes, minimized user interventions, reduced risk of contamination, and increased productivity and reproducibility of the results.

The other advantages of the device due to its integrity are facilitated portability and less occupied space by the device. The device requires less equipment and parts; consequently, the final cost to manufacture the device and even to produce the bioengineered tissues/organs decreases and requires less space. Self-sterilization is another unique feature of this device. The self-sterilization system is designed such that it has access to all valves, conduits, and sterilizes the mentioned components using sterilizing sources such as, but not limited to, ethylene oxide and/or ozone gas. The device is fully automated and configured to bioengineer various tissues/organs with different sizes (e.g., from rat to human sizes). The device could be functioned as an incubator providing the user-defined temperature and also able to perform different user-defined protocols for decellularization, tissue sterilization, and recellularization.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions.

Although specific terms may be employed herein, they are used only in generic and descriptive sense and not for purposes of limitation. Accordingly, the present invention is not limited to the specific embodiments illustrated herein. While the above is a complete description of the preferred embodiments of the invention, various alternatives, modifications, and equivalents may be used. Therefore, the above description and the examples should not be taken as limiting the scope of the invention, which is defined by the appended claims.

What is claimed is:

1. An automated device for tissue and organ engineering, comprising:
   a main chamber having at least one solution inlet, at least one solution outlet, wherein the main chamber is configured to receive and culture tissue in a sterile and sealed environment;
   at least one solution chamber fluidly connected to the main chamber through at least one solution conduit, at least one solution valve, at least one solution pump, and the at least one solution inlet, wherein the at least one solution chamber is configured to contain liquid solution for decellularization and tissue sterilization processes;
   at least one waste chamber fluidly connected to the main chamber through at least one waste conduit, at least one waste pump, at least one waste valve, and the at least one solution outlet, wherein the at least one waste chamber is configured to receive waste liquid from the main chamber and the at least one solution chamber;
   a sterilizing system which includes at least one sterilization source containing at least one of sterilizing gas and sterilizing liquid, wherein the at least one sterilization source is fluidly connected to the at least one solution conduit, and the at least one waste conduit through at least one sterilizing valve, wherein the sterilizing gas is at least any one of ozone and ethylene oxide;
   a controller configured to control the at least one solution valve, the at least one waste valve, the at least one sterilizing valve, the at least one solution pump, and the at least one waste pump, and
   a user interface in communication with the controller configured to allow a user to input protocol to perform decellularization, tissue sterilization, recellularization, and self-sterilization processes, wherein the controller is configured to automatically implement the protocol for performing the decellularization, tissue sterilization, recellularization, and self-sterilization processes.

2. The device of claim 1, wherein the tissue is perfused through one or more embedded ports based on the input protocol.

3. The device of claim 1, wherein the at least one solution chamber is at least one of a carboy and a syringe.

4. The device of claim 1, wherein the liquid solution includes at least any one of phosphate-buffered saline (PBS); and sodium dodecyl sulfate (SDS), for decellularization process.

5. The device of claim 1, wherein the liquid solution includes at least one of penicillin and streptomycin for the tissue sterilization process.

6. The device of claim 1, wherein the at least one solution valve is a solenoid pinch-type valve.

7. The device of claim 1, wherein the at least one solution pump is a peristaltic pump.

8. The device of claim 1, wherein the at least one solution outlet, the at least one solution conduit, the at least one solution pump, the at least one solution valve, and the at least one solution inlet form a closed loop for continuously circulating the liquid solution within the main chamber for effectively perfusing the tissue.

9. The device of claim 1, wherein the main chamber is transparent and autoclavable and could comprise different ports and sensors including pH and O2.

10. The device of claim 1, also comprises at least a temperature sensor to measure the temperature inside the main chamber and a temperature control system to adjust the temperature inside the main chamber based on a user-defined value and the temperature sensor measurement.

11. The device of claim 1, wherein the chambers and the conduits of the device are autoclavable, and wherein different tissues or organs of various sizes are processed using the device.

12. An automated device for tissue and organ engineering, comprising:
   a main chamber having at least one medium inlet, at least one medium outlet, at least one gas inlet, and at least one gas outlet, wherein the main chamber is configured to receive and culture tissue in a sterile and sealed environment;
   at least one medium chamber fluidly connected to the main chamber through at least one medium conduit, at least one medium valve, at least one medium pump, and the at least one medium inlet, wherein the at least one medium chamber is configured to contain liquid medium for recellularization processes, wherein the at least one medium outlet, the at least one medium conduit, the at least one medium pump, the at least one medium valve, and the at least one medium inlet form a closed loop for continuously circulating the liquid medium within the main chamber for effectively perfusing the tissue;

at least one waste chamber fluidly connected to the main chamber through at least one waste conduit, at least one waste pump, at least one waste valve, and the at least one medium outlet, wherein the at least one waste chamber is configured to receive a waste liquid from the main chamber and the at least one medium chamber;

a sterilizing system which includes at least one sterilization source containing at least one of sterilizing gas or sterilizing liquid, wherein the at least one sterilization source is fluidly connected to the at least one medium conduit, and at least one waste conduit through at least one sterilizing valve;

a controller configured to control the at least one medium valve, the at least one waste valve, the at least one sterilizing valve, the at least one medium pump, and the at least one waste pump, and a user interface in communication with the controller configured to allow a user to input protocol to perform decellularization, tissue sterilization, recellularization, and self-sterilization process, wherein the controller is configured to automatically implement the protocol for performing the decellularization, tissue sterilization, recellularization, and self-sterilization process.

13. The device of claim 12, wherein the tissue is perfused through one or more embedded ports based on the input protocol.

14. The device of claim 12, further comprises at least one gas source fluidly connected to the main chamber through at least one gas conduit and at least one gas inlet, wherein an inlet gas valve controls flow of gas into the main chamber, wherein the gas is at least any one of oxygen, carbon dioxide, and nitrogen, and wherein the gas source is at least any one of a gas generator, a capsule, and a gas compressor, and wherein at least one gas conduit discharges gas from the main chamber through at least one gas outlet.

15. The device of claim 12, wherein the liquid solution includes at least any one of phosphate-buffered saline (PBS); and sodium dodecyl sulfate (SDS), for decellularization process.

16. The device of claim 12, wherein the liquid solution includes at least one of penicillin and streptomycin for tissue sterilization process.

17. The device of claim 12, further comprises at least one gas source fluidly connected to the main chamber through at least one inlet gas conduit, wherein an inlet gas valve controls the flow of gas into the main chamber.

18. The device of claim 17, wherein the gas is at least any one of oxygen, carbon dioxide, and nitrogen.

19. The device of claim 17, wherein the at least one gas source is at least any one of a gas generator, a capsule, and a gas compressor.

20. The device of claim 12, wherein the at least one medium inlet and the at least one medium outlet of the main chamber form a closed loop for continuously circulating a liquid solution within the main chamber for effectively perfusing the tissue.

* * * * *